(12) United States Patent
Viti et al.

(10) Patent No.: US 12,112,471 B2
(45) Date of Patent: *Oct. 8, 2024

(54) SYSTEMS AND METHODS FOR MULTI-LABEL SEGMENTATION OF CARDIAC COMPUTED TOMOGRAPHY AND ANGIOGRAPHY IMAGES USING DEEP NEURAL NETWORKS

(71) Applicant: GE Precision Healthcare LLC, Milwaukee, WI (US)

(72) Inventors: Mario Viti, Paris (FR); Faycal El Hanchi El Amrani, Paris (FR); Nicolas Gogin, Chatenay Malabry (FR); Celine Pruvot, Buc (FR)

(73) Assignee: GE PRECISION HEALTHCARE LLC, Milwaukee, WI (US)

( * ) Notice: Subject to any disclaimer, the term of this patent is extended or adjusted under 35 U.S.C. 154(b) by 93 days.

This patent is subject to a terminal disclaimer.

(21) Appl. No.: 17/456,145

(22) Filed: Nov. 22, 2021

(65) Prior Publication Data

US 2022/0084198 A1 Mar. 17, 2022

Related U.S. Application Data

(63) Continuation of application No. 16/653,906, filed on Oct. 15, 2019, now Pat. No. 11,205,264.

(51) Int. Cl.
*G06T 7/11* (2017.01)
*A61B 5/00* (2006.01)
(Continued)

(52) U.S. Cl.
CPC .......... *G06T 7/0012* (2013.01); *A61B 5/7264* (2013.01); *G06N 3/045* (2023.01);
(Continued)

(58) Field of Classification Search
CPC .................................................. G06T 7/0012
See application file for complete search history.

(56) References Cited

U.S. PATENT DOCUMENTS

2017/0258433 A1* 9/2017 Gulsun ................ A61B 6/5217
2017/0296055 A1 10/2017 Gardner et al.
(Continued)

OTHER PUBLICATIONS

Kolossvary, M. et al., "Plaque imaging with CT—a comprehensive review on coronary CT angiography based risk assessment," Cardiovascular Diagnosis and Therapy, vol. 7, No. 5, Oct. 2017, 18 pages.
(Continued)

*Primary Examiner* — Oneal R Mistry
(74) *Attorney, Agent, or Firm* — McCoy Russell LLP

(57) ABSTRACT

Methods and systems are provided for detecting coronary lesions in 3D cardiac computed tomography and angiography (CCTA) images using deep neural networks. In an exemplary embodiment, a method for detecting coronary lesions in 3D CCTA images comprises, acquiring a 3D CCTA image of a coronary tree, mapping the 3D CCTA image to a multi-label segmentation map with a trained deep neural network, generating a plurality of 1D parametric curves for a branch of the coronary tree using the multi-label segmentation map, determining a location of a lesion in the branch of the coronary tree using the plurality of 1D parametric curves, and determining a severity score for the lesion based on the plurality of 1D parametric curves.

18 Claims, 7 Drawing Sheets

(51) Int. Cl.
  *G06N 3/045*   (2023.01)
  *G06N 3/08*   (2023.01)
  *G06T 7/00*   (2017.01)
  *G06T 17/00*   (2006.01)

(52) U.S. Cl.
  CPC ............... *G06N 3/08* (2013.01); *G06T 7/11* (2017.01); *G06T 17/005* (2013.01); *G06T 2207/10081* (2013.01); *G06T 2207/30048* (2013.01); *G06T 2207/30096* (2013.01); *G06T 2207/30101* (2013.01)

(56) References Cited

U.S. PATENT DOCUMENTS

| | | | |
|---|---|---|---|
| 2017/0325770 A1* | 11/2017 | Edic | A61B 6/503 |
| 2019/0156554 A1 | 5/2019 | Aben et al. | |
| 2019/0318476 A1* | 10/2019 | Isgum | G16H 50/50 |
| 2019/0336096 A1* | 11/2019 | Itu | G16H 50/50 |
| 2020/0034968 A1* | 1/2020 | Freiman | G06T 17/005 |
| 2020/0113449 A1* | 4/2020 | Freiman | A61B 5/026 |
| 2020/0222018 A1 | 7/2020 | van Walsum et al. | |
| 2020/0281562 A1 | 9/2020 | Haase et al. | |
| 2021/0110533 A1 | 4/2021 | Viti et al. | |

OTHER PUBLICATIONS

Preik, M. et al., "A Recurrent CNN for Automatic Detection and Classification of Coronary Artery Plaque and Stenosis in Coronary CT Angiography," IEEE Transactions on Medical Imaging, vol. 38, No. 7, Jul. 2019, 11 pages.

\* cited by examiner

FIG. 8
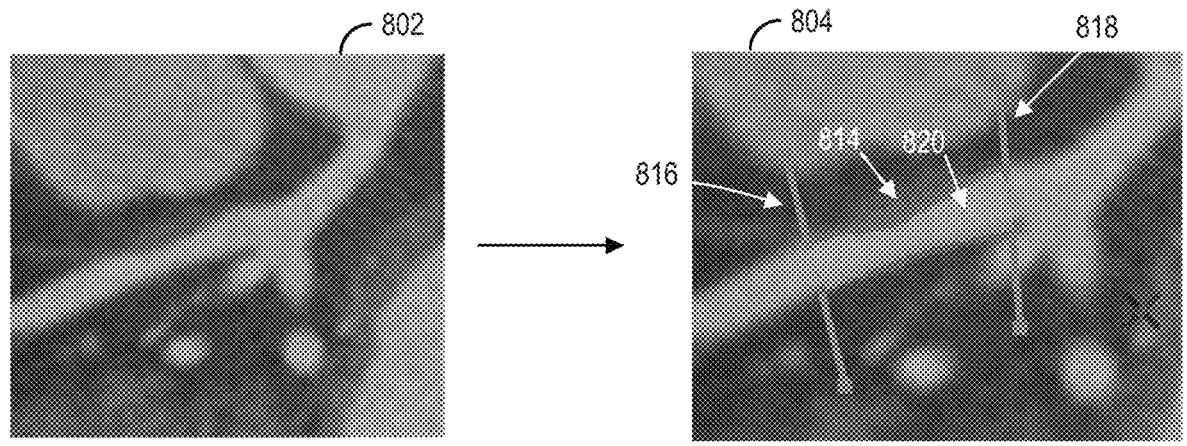
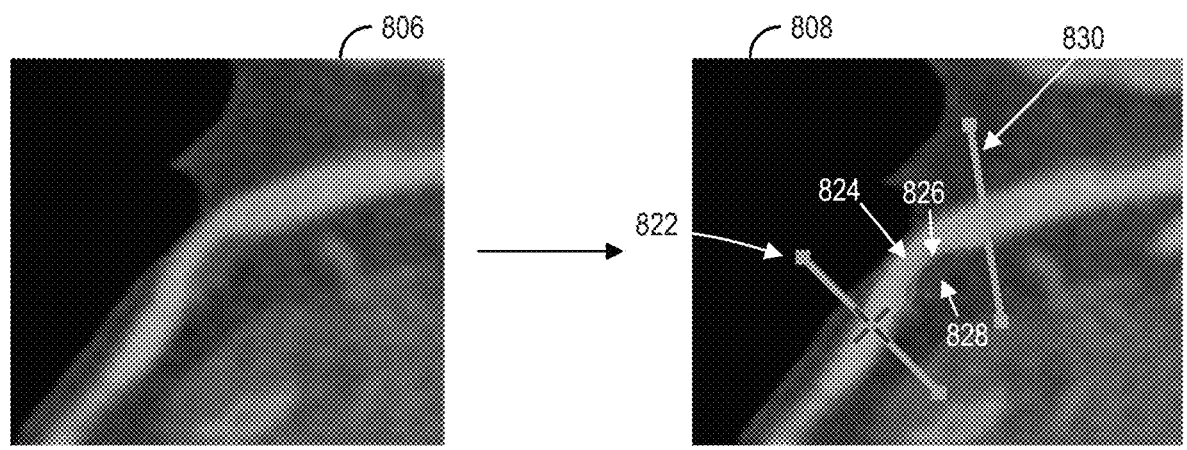
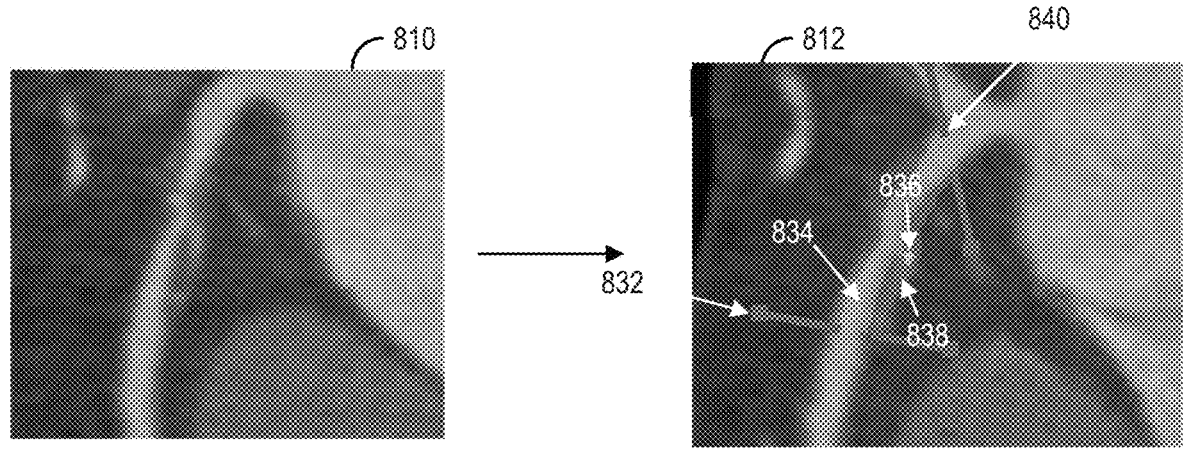

SYSTEMS AND METHODS FOR MULTI-LABEL SEGMENTATION OF CARDIAC COMPUTED TOMOGRAPHY AND ANGIOGRAPHY IMAGES USING DEEP NEURAL NETWORKS

CROSS REFERENCE TO RELATED APPLICATIONS

The present application claims priority to U.S. non-provisional application Ser. No. 16/653,906, entitled "SYSTEMS AND METHODS FOR MULTI-LABEL SEGMENTATION OF CARDIAC COMPUTED TOMOGRAPHY AND ANGIOGRAPHY IMAGES USING DEEP NEURAL NETWORKS", filed on Oct. 15, 2019. The entire contents of the above-listed application are hereby incorporated by reference for all purposes.

TECHNICAL FIELD

Embodiments of the subject matter disclosed herein relate to analyzing cardiac computed tomography and angiography (CCTA) images, and more particularly, to systems and methods for multi-label segmentation of CCTA images using deep neural networks.

BACKGROUND

Today, the assessment of coronary lesions is done manually by clinicians. The review of cardiac computed tomography and angiography (CCTA) images to determine the condition of a the coronary arteries is a tedious task because the coronary arteries are nonplanar, three-dimensional (3D) structures, and the clinician may need to rely on advanced visualization tools to view the 3D structures in multiple perspective views, such as along a longitudinal axis of a coronary artery, along a cross section of a coronary artery etc., to assess the presence/severity of a coronary lesion. As a consequence, the identification of coronary lesions and the assessment of the type/severity of coronary lesions is labor intensive and time consuming. Further detection and assessment of coronary lesions in the manner described above may also produce inconsistent diagnoses, especially when the assessment on CCTA images is compared to other imaging modalities such as intracardiac ultrasound, optical coherence tomography and angiography (OCTA), etc. Thus, exploring techniques for rapidly and accurately detecting coronary lesions using CCTA images, and determining a type/severity of the detected lesions, is generally desired.

SUMMARY

The present disclosure at least partially addresses the issues described above. In one embodiment, a method for detecting coronary lesions in 3D CCTA images comprises, acquiring a 3D CCTA image of a coronary tree mapping the 3D CCTA image to a multi-label segmentation map with a trained deep neural network, generating a plurality of one-dimensional (1D) parametric curves for a branch of the coronary tree using the multi-label segmentation map, determining a location of a lesion in the branch of the coronary tree using the plurality of 1D parametric curves, and determining a severity score for the lesion based on the plurality of 1D parametric curves. In this way, automatic and robust detection of coronary lesions may be enabled.

The above advantages and other advantages, and features of the present description will be readily apparent from the following Detailed Description when taken alone or in connection with the accompanying drawings. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Various aspects of this disclosure may be better understood upon reading the following detailed description and upon reference to the drawings in which:

FIG. 8 shows examples of CCTA images with corresponding multi-label segmentation maps, according to an exemplary embodiment of the current disclosure.

Figure 1:
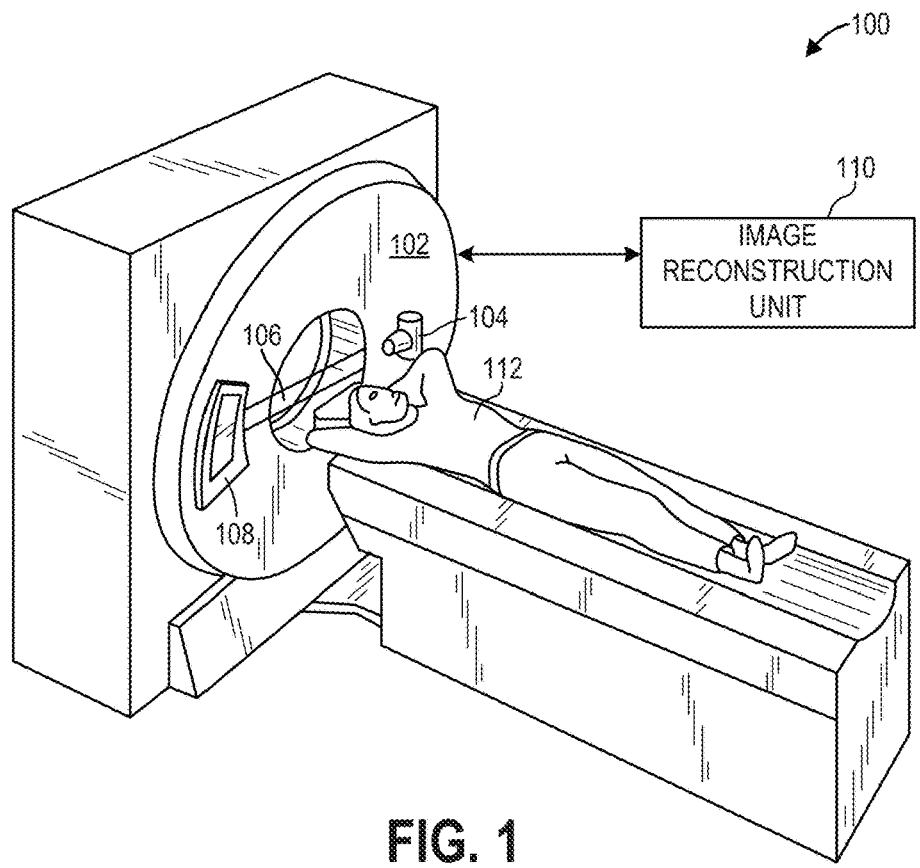
FIG. 1 is an illustration of an exemplary embodiment of a cardiac computed tomography and angiography (CCTA) imaging system.

The drawings illustrate specific aspects of the described systems and methods for detecting coronary lesions using 3D CCTA images and deep neural networks. Together with the following description, the drawings demonstrate and explain the structures, methods, and principles described herein. In the drawings, the size of components may be exaggerated or otherwise modified for clarity. Well-known structures, materials, or operations are not shown or described in detail to avoid obscuring aspects of the described components, systems and methods.

DETAILED DESCRIPTION

The following description relates to various embodiments for determining 3D multi-label segmentation maps from 3D CCTA images using deep neural networks. The disclosure further relates to automatically detecting coronary lesions using the 3D multi-label segmentation maps. In one embodiment, 3D CCTA images acquired by CCTA imaging system 100, shown in FIG. 1, or imaging system 200, shown in FIG. 2, may be analyzed for the presence of coronary lesions by CCTA image processing system 302, shown in FIG. 3.

Figure 4:
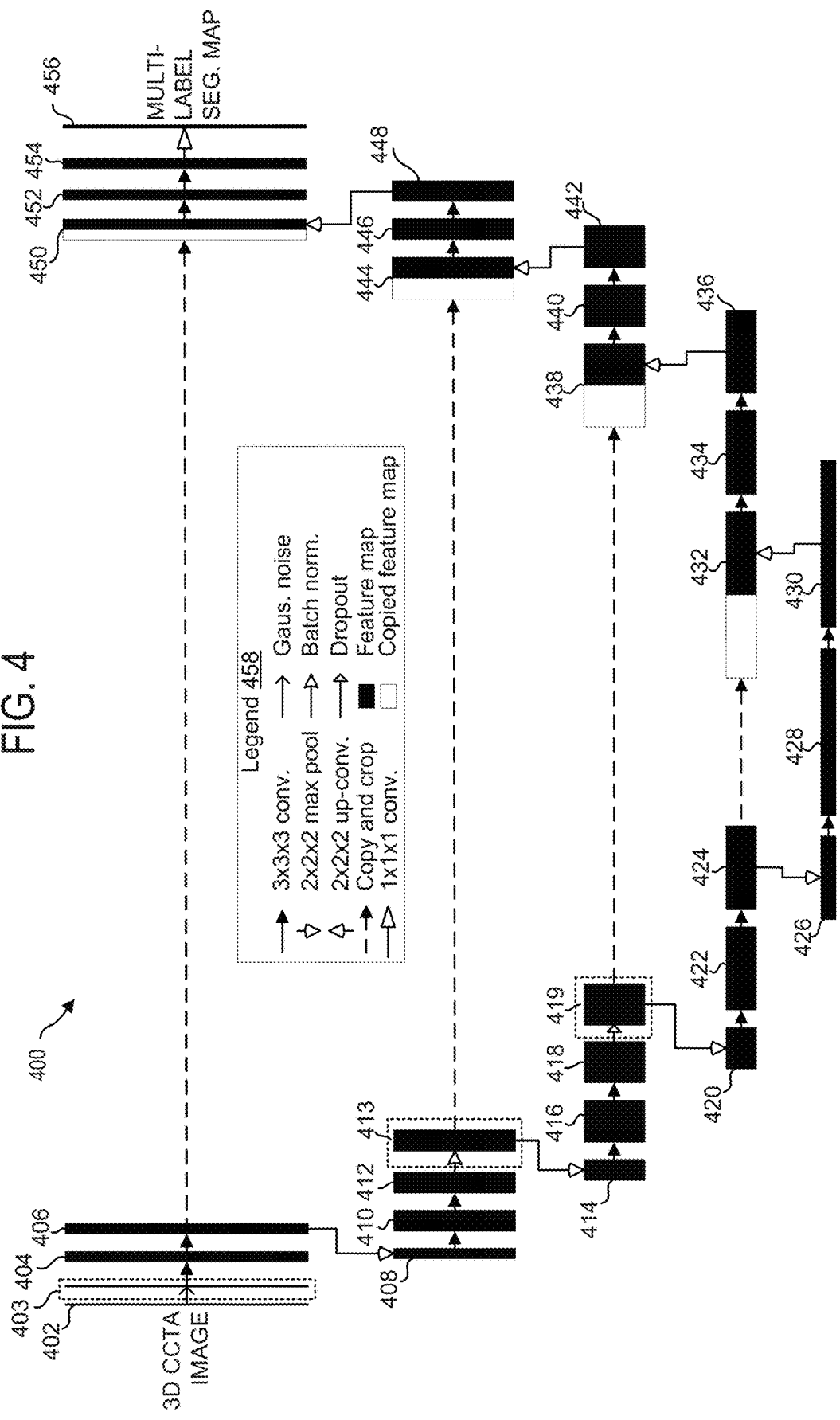
FIG. 4 is a schematic diagram illustrating an exemplary architecture of a deep neural network which can be used in the system of FIG. 3, according to an exemplary embodiment.
Figure 5:
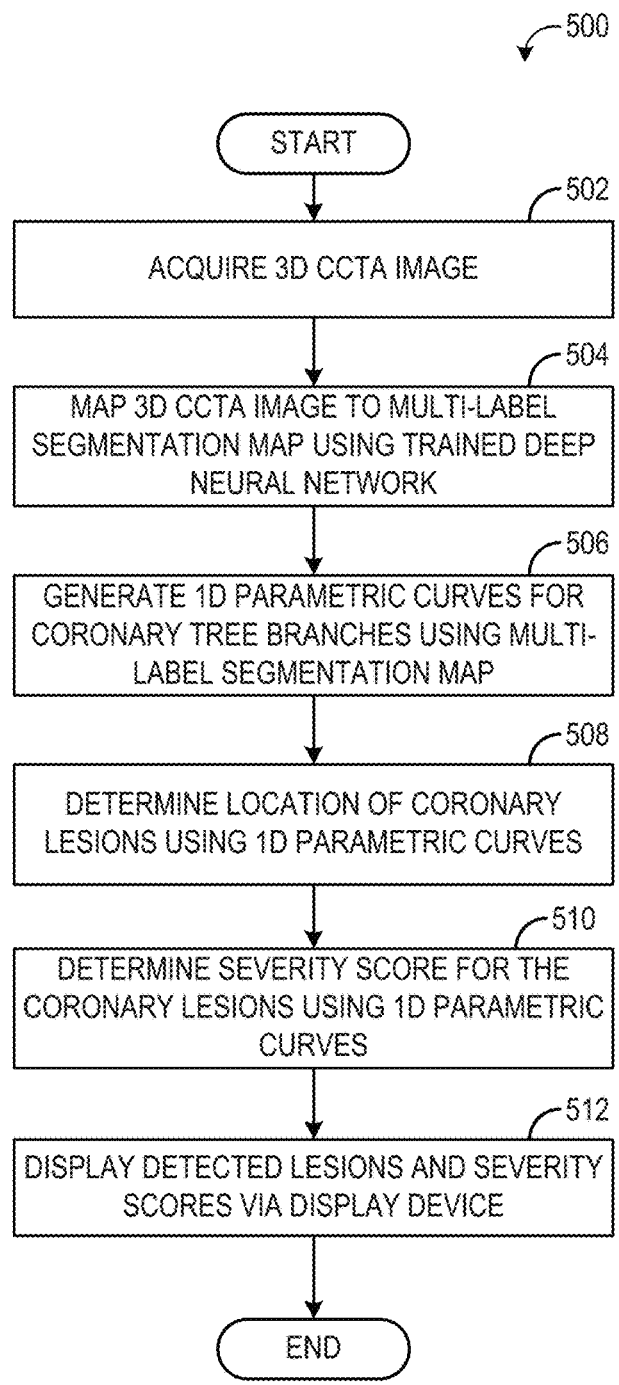
FIG. 5 is a flow chart illustrating a method for detecting coronary lesions in 3D CCTA images using deep neural networks, according to an exemplary embodiment.

CCTA image processing system 302 may execute one or more steps of method 500, shown in FIG. 5, which includes mapping the acquired 3D CCTA image to a multi-label segmentation map using convolutional neural network 400, shown in FIG. 4, and using the multi-label segmentation map to determine a plurality of 1D parametric curves for each branch of the coronary tree. An example of 1D parametric curves which may be generated using multi-label segmentation maps are shown in FIG. 7, while examples of CCTA images and corresponding multi-label segmentation maps are shown in FIG. 8. The plurality of 1D parametric curves may be used to detect one or more coronary lesions, and to assess a severity of the one or more coronary lesions. The convolutional neural network 400 used to map the 3D CCTA images to multi-label segmentation maps may be trained using method 600, shown in FIG. 6, wherein training data pairs comprising 3D CCTA images and corresponding ground truth multi-label segmentation maps are used to adjust one or more parameters of the deep neural network.

As used herein, 3D CCTA images refer to three-dimensional CCTA images comprising a measured volume. 3D CCTA images comprise imaging data for three distinct spatial dimensions. 3D CCTA images may comprise a plurality of voxels, or units of volume, which may be contrasted with pixels of two-dimensional images, wherein pixels comprise units of area. Similarly, 3D multi-label segmentation maps comprise label data for one or more voxels of the 3D CCTA images, and therefore may comprise labels for voxels arranged in a three-dimensional space.

As used herein, 1D parametric curves refer to parameters or values measured along a single dimension, such as length, or angle. A 1D parametric curve shows a parameter as a function of a single spatial dimension, and may be illustrated graphically as a series of values of a parameter at each of a plurality of set intervals along the spatial dimension.

FIG. 1 illustrates an exemplary CCTA imaging system 100 configured to allow fast and iterative image reconstruction of the coronary arteries of a heart. Particularly, the CCTA imaging system 100 is configured to image a heart of subject 112. In one embodiment, the CCTA imaging system 100 includes a gantry 102, which in turn, may include at least one x-ray radiation source 104 configured to project a beam of x-ray radiation 106 for use in imaging the subject 112. Specifically, the x-ray radiation source 104 is configured to project the x-rays 106 towards a detector array 108 positioned on the opposite side of the gantry 102. Although FIG. 1 depicts only a single x-ray radiation source 104, in certain embodiments, multiple x-ray radiation sources and detectors may be employed to project a plurality of x-rays 106 for acquiring projection data corresponding to the patient at different energy levels. In some embodiments, the x-ray radiation source 104 may enable dual-energy gemstone spectral imaging (GSI) by rapid kVp switching. In some embodiments, the x-ray detector employed is a photon-counting detector which is capable of differentiating x-ray photons of different energies. In other embodiments, two sets of x-ray tube-detector are used to generate dual-energy projections, with one set at low-kVp and the other at high-kVp. It should thus be appreciated that the methods described herein may be implemented with single energy acquisition techniques as well as dual energy acquisition techniques.

In certain embodiments, the CCTA imaging system 100 further includes an image reconstruction unit 110, configured to reconstruct images of a target volume of the subject 112 using an iterative or analytic image reconstruction method. For example, the image reconstruction unit 110 may use an analytic image reconstruction approach such as filtered backprojection (FBP) to reconstruct images of a target volume of the patient. As another example, the image reconstruction unit 110 may use an iterative image reconstruction approach such as advanced statistical iterative reconstruction (ASIR), conjugate gradient (CG), maximum likelihood expectation maximization (MLEM), model-based iterative reconstruction (MBIR), and so on, to reconstruct images of a target volume of the subject 112. In some embodiments, the image processor unit 110 may use both an analytic image reconstruction approach such as FBP in addition to an iterative image reconstruction approach.

In some known CCTA imaging system configurations, a radiation source projects a cone-shaped beam which is collimated to lie within an X-Y-Z plane of a Cartesian coordinate system and generally referred to as an "imaging plane." The radiation beam passes through an object being imaged, such as the patient or subject 112. The beam, after being attenuated by the object, impinges upon an array of radiation detectors. The intensity of the attenuated radiation beam received at the detector array is dependent upon the attenuation of a radiation beam by the object. Each detector element of the array produces a separate electrical signal that is a measurement of the beam attenuation at the detector location. The attenuation measurements from all the detectors are acquired separately to produce a transmission profile.

In some CCTA imaging systems, the radiation source and the detector array are rotated with a gantry within the imaging plane and around the object to be imaged such that an angle at which the radiation beam intersects the object constantly changes. A group of radiation attenuation measurements, i.e., projection data, from the detector array at one gantry angle is referred to as a "view." A "scan" of the object includes a set of views made at different gantry angles, or view angles, during one revolution of the radiation source and detector.

The projection data is processed to reconstruct an image that corresponds to a two-dimensional slice taken through the object. One method for reconstructing an image from a set of projection data is referred to in the art as the filtered backprojection technique. Transmission and emission tomography reconstruction techniques also include statistical iterative methods such as maximum likelihood expectation maximization (MLEM) and ordered-subsets expectation-reconstruction techniques as well as iterative reconstruction techniques. This process converts the attenuation measurements from a scan into integers called "CT numbers" or "Hounsfield units," which are used to control the brightness of a corresponding pixel on a display device.

To reduce the total scan time, a "helical" scan may be performed. To perform a "helical" scan, the patient is moved while the data for the prescribed number of slices is acquired. Such a system generates a single helix from a cone beam helical scan. The helix mapped out by the cone beam yields projection data from which images in each prescribed slice may be reconstructed.

As used herein, the phrase "reconstructing an image" is not intended to exclude embodiments of the present invention in which data representing an image is generated but a viewable image is not. Therefore, as used herein the term "image" broadly refers to both viewable images and data representing a viewable image. However, many embodiments generate (or are configured to generate) at least one viewable image.

Figure 2:
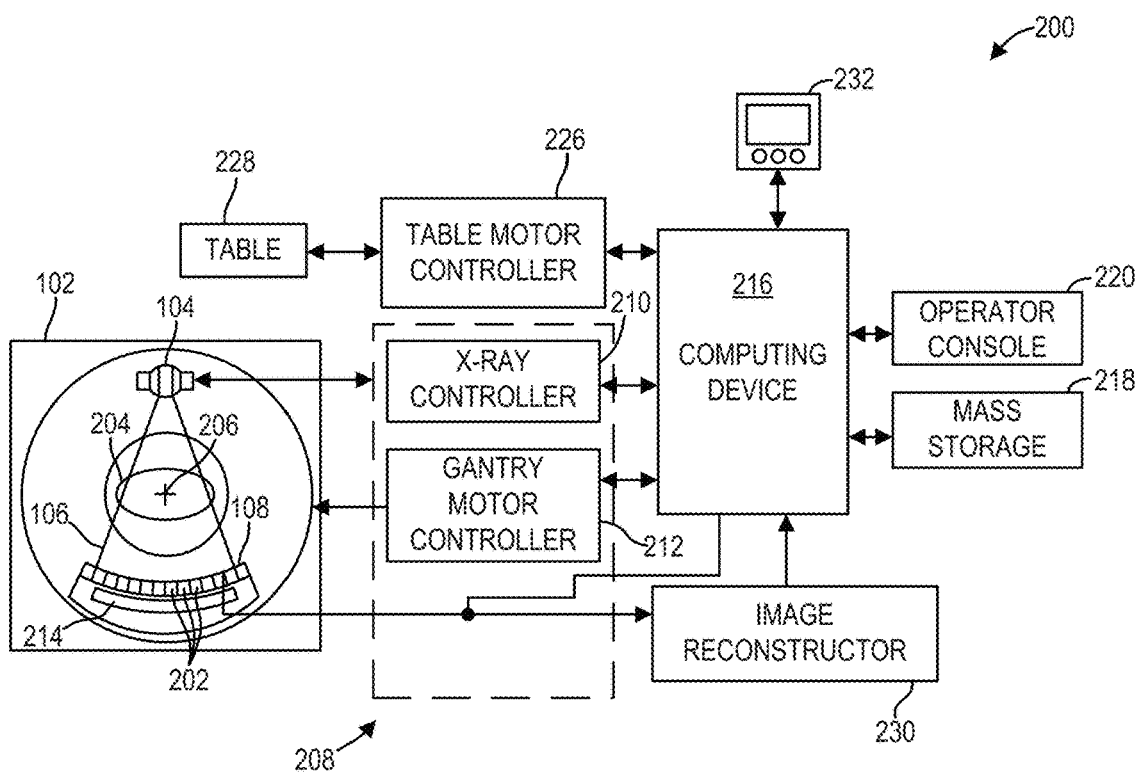
FIG. 2 shows a block diagram of an exemplary embodiment of an imaging system.

FIG. 2 illustrates an exemplary imaging system 200 similar to the CCTA imaging system 100 of FIG. 1. In one embodiment, the imaging system 200 includes the detector array 108 (see FIG. 1). The detector array 108 further includes a plurality of detector elements 202 that together sense the x-ray beams 106 (see FIG. 1) that pass through a subject 204 such as a patient to acquire corresponding projection data. Accordingly, in one embodiment, the detector array 108 is fabricated in a multi-slice configuration including the plurality of rows of cells or detector elements 202. In such a configuration, one or more additional rows of the detector elements 202 are arranged in a parallel configuration for acquiring the projection data.

In certain embodiments, the imaging system 200 is configured to traverse different angular positions around the subject 204 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

As the x-ray source 104 and the detector array 108 rotate, the detector array 108 collects data of the attenuated x-ray beams. The data collected by the detector array 108 undergoes pre-processing and calibration to condition the data to represent the line integrals of the attenuation coefficients of the scanned subject 204. The processed data are commonly called projections.

In dual or multi-energy imaging, two or more sets of projection data are typically obtained for the imaged object at different tube kilovoltage (kVp) levels, which change the maximum and spectrum of energy of the incident photons comprising the emitted x-ray beams or, alternatively, at a single tube kilovoltage (kVp) level or spectrum with an energy resolving detector of the detector array 108.

The acquired sets of projection data may be used for basis material decomposition (BMD). During BMD, the measured projections are converted to a set of material-density projections. The material-density projections may be reconstructed to form a pair or a set of material-density map or image of each respective basis material, such as bone, soft tissue, and/or contrast agent maps. The density maps or images may be, in turn, associated to form a volume rendering of the basis material, for example, bone, soft tissue, and/or contrast agent, in the imaged volume.

In CCTA imaging, a radio contrast agent is administered to a patient prior to imaging, the radiocontrast agent enables differentiation between vessel walls and lumen to be made, as the x-ray beams passing through radiocontrast agent are differently attenuated than those passing through other materials, such as plaques or vessel walls.

Once reconstructed, the basis material image produced by the imaging system 200 reveals internal features of the subject 204, expressed in the densities of the two basis materials. The density image may be displayed to show these features. In traditional approaches to diagnosis medical conditions, such as disease states, and more generally of medical events, a radiologist or physician would consider a hard copy or display of the density image to discern characteristic features of interest. Such features might include lesions, sizes and shapes of particular anatomies or organs, and other features that would be discernable in the image based upon the skill and knowledge of the individual practitioner.

In one embodiment, the imaging system 200 includes a control mechanism 208 to control movement of the components such as rotation of the gantry 102 and the operation of the x-ray radiation source 104. In certain embodiments, the control mechanism 208 further includes an x-ray controller 210 configured to provide power and timing signals to the radiation source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214 configured to sample analog data received from the detector elements 202 and convert the analog data to digital signals for subsequent processing. The data sampled and digitized by the DAS 214 is transmitted to a computer or computing device 216. In one example, the computing device 216 stores the data in a storage device 218. The storage device 218, for example, may include a hard disk drive, a floppy disk drive, a compact disk-read/write (CD-R/W) drive, a Digital Versatile Disc (DVD) drive, a flash drive, and/or a solid-state storage drive.

Additionally, the computing device 216 provides commands and parameters to one or more of the DAS 214, the x-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown) or a touchscreen to allow the operator to specify the commands and/or scanning parameters.

Although FIG. 2 illustrates only one operator console 220, more than one operator console may be coupled to the imaging system 200, for example, for inputting or outputting system parameters, requesting examinations, and/or viewing images. Further, in certain embodiments, the imaging system 200 may be coupled to multiple display devices, printers, workstations, and/or similar devices located either locally or remotely, for example, within an institution or hospital, or in an entirely different location via one or more configurable wired and/or wireless networks such as the Internet and/or virtual private networks.

The computing device 216 uses the operator-supplied and/or system-defined commands and parameters to operate a table motor controller 226, which in turn, may control a table 228 which may comprise a motorized table. Particularly, the table motor controller 226 moves the table 228 for appropriately positioning the subject 204 in the gantry 102 for acquiring projection data corresponding to the target volume of the subject 204.

As previously noted, the DAS 214 samples and digitizes the projection data acquired by the detector elements 202. Subsequently, an image reconstructor 230 uses the sampled and digitized x-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the imaging system 200 and instead the computing device 216 may perform one or more functions of the image reconstructor 230. Moreover, the image reconstructor 230 may be located locally or remotely, and may be operatively connected to the imaging system 200 using a wired or wireless network. Particularly, one exemplary embodiment may use computing resources in a "cloud" network cluster for the image reconstructor 230.

In one embodiment, the image reconstructor 230 stores the images reconstructed in the storage device 218. Alternatively, the image reconstructor 230 transmits the reconstructed images to the computing device 216 for generating useful patient information for diagnosis and evaluation. In certain embodiments, the computing device 216 transmits the reconstructed images and/or the patient information to a display 232 communicatively coupled to the computing device 216 and/or the image reconstructor 230.

The various methods and processes described further herein may be stored as executable instructions in non-transitory memory on a computing device in imaging system 200.

In one embodiment, the display 232 allows the operator to evaluate the imaged anatomy. The display 232 may also allow the operator to select a volume of interest (VOI) and/or request patient information, for example, via a graphical user interface (GUI) for a subsequent scan or processing.

Figure 3:
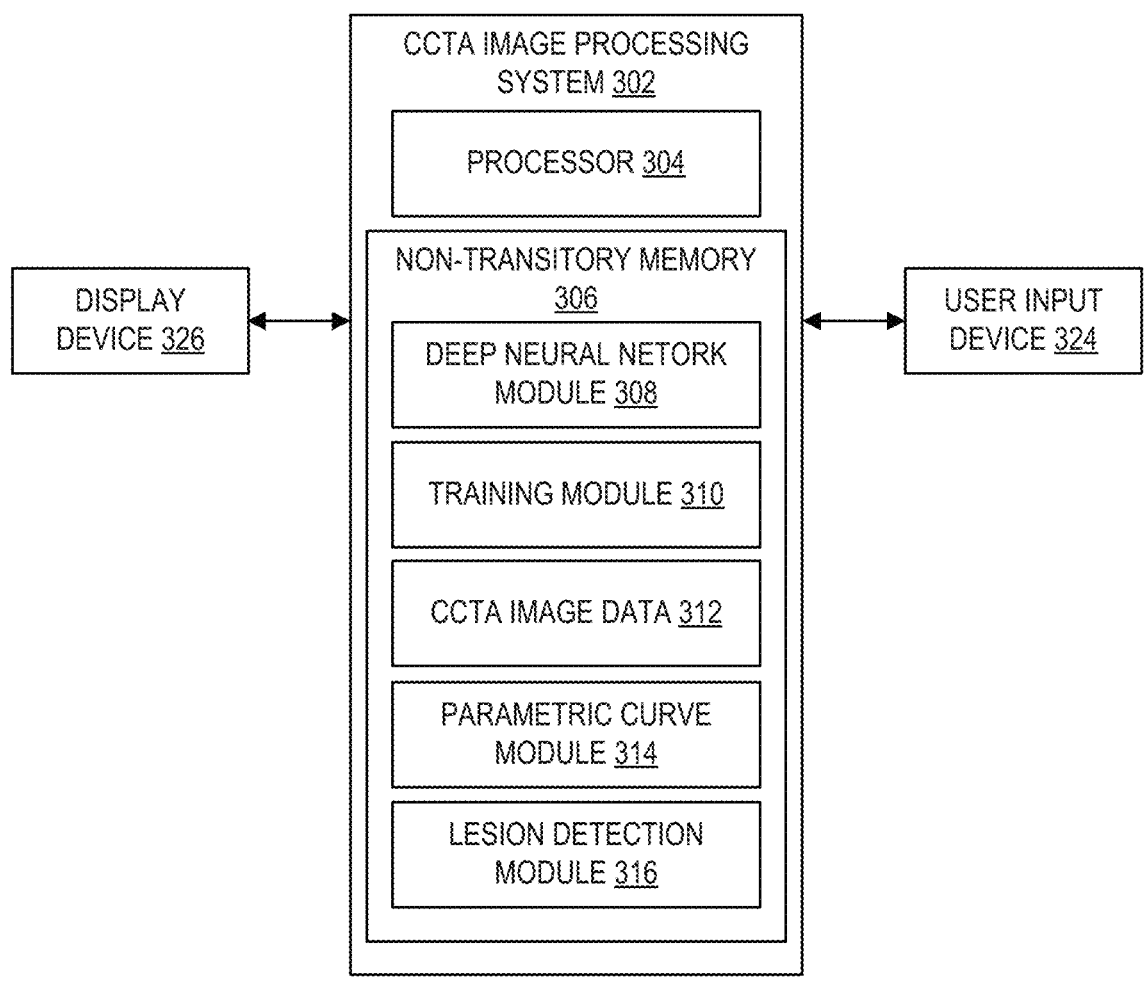
FIG. 3 shows an exemplary embodiment of a CCTA image processing system.

Referring to FIG. 3, an exemplary embodiment of a CCTA image processing system 302 is shown. In some embodiments, CCTA image processing system 302 may be communicatively coupled to one or more of CCTA imaging system 100, or imaging system 200, shown in FIGS. 1 and 2, respectively. In some embodiments CCTA image processing system 302 is incorporated into the CCTA imaging system. In some embodiments, at least a portion of CCTA image processing system 302 is disposed at a device (e.g., edge device, server, etc.) communicably coupled to the CCTA imaging system via wired and/or wireless connections. In some embodiments, at least a portion of CCTA image processing system 302 is disposed at a separate device (e.g., a workstation) which can receive images from the CCTA imaging system or from a storage device which stores the images generated by the CCTA imaging system. CCTA image processing system 302 comprises processor 304, configured to execute instructions stored in non-transitory memory 306. CCTA image processing system 302 is communicatively coupled to display device 326, and user input device 324, which may enable a user to view and input/interact with data stored within CCTA image processing system 302, respectively.

CCTA image processing system 302 includes a processor 304 configured to execute machine readable instructions stored in non-transitory memory 306. Processor 304 may be single core or multi-core, and the programs executed thereon may be configured for parallel or distributed processing. In some embodiments, the processor 304 may optionally include individual components that are distributed throughout two or more devices, which may be remotely located and/or configured for coordinated processing. In some embodiments, one or more aspects of the processor 304 may be virtualized and executed by remotely-accessible networked computing devices configured in a cloud computing configuration.

Non-transitory memory 306 may store deep neural network module 308, training module 310, CCTA image data 312, parametric curve module 314, and lesion detection module 316. Non-transitory memory may comprise computer-readable media (CRM) that stores data in the presence or absence of power. In some embodiments, the non-transitory memory 306 may include components disposed at two or more devices, which may be remotely located and/or configured for coordinated processing. In some embodiments, one or more aspects of the non-transitory memory 306 may include remotely-accessible networked storage devices configured in a cloud computing configuration.

Deep neural network module 308 may include one or more deep neural networks, comprising a plurality of weights and biases, activation functions, and instructions for implementing the one or more deep neural networks to receive 3D CCTA images and map the 3D CCTA images to 3D multi-label segmentation maps. For example, deep neural network module 308 may store parameters of, and instructions for implementing, a neural network, such as the convolutional neural network (CNN) 400 illustrated in FIG. 4. Deep neural network module 308 may include trained and/or untrained neural networks and may further include various data, such as metadata pertaining to the one or more deep neural networks stored in deep neural network module 308.

Non-transitory memory 306 may further include training module 310, which comprises instructions for training one or more of the deep neural networks stored in deep neural network module 308. Training module 310 may include one or more gradient descent algorithms, one or more loss functions, one or more training data selection criteria, one or more backpropagation algorithms, etc. Training module 310 may include instructions that, when executed by processor 304, cause CCTA image processing system 302 to conduct one or more of the steps of method 600, discussed in more detail below. In one example, training module 310 includes instructions for selecting training data pairs from CCTA image data 312, which comprise pairs of 3D CCTA images of coronary trees, such as may be acquired via CCTA imaging system 100, and ground truth 3D multi-label segmentation maps comprising ground truth labels for each voxel of the 3D CCTA image, wherein the labels are of one or more anatomical classes, including lumen, media, fibrous cap, lipid core, calcium, external tissue, and undetermined. In some embodiments, the ground truth multi-label segmentation maps comprise higher spatial resolution than the corresponding input CCTA images (that is, for a particular training data pair, a number of voxels in the ground truth multi-label segmentation map is greater than the number of voxels in the corresponding input CCTA images), thereby enabling training of a deep neural network to produce multi-label segmentation maps of a higher spatial resolution than the native resolution of the input CCTA images (i.e., super resolution). The training data pairs selected by training module 310 may be used to conduct supervised learning of one or more deep neural networks stored in deep neural network module 308. In some embodiments, the training module 310 is not disposed at the CCTA image processing system 302.

Non-transitory memory 306 further includes CCTA image data 312. In some embodiments, CCTA image data 312 includes a plurality of 3D CCTA images of coronary trees, which may be indexed by one or more pieces of metadata pertaining to the 3D CCTA images. In some embodiments, CCTA image data 312 may further include a plurality of training data pairs, comprising 3D CCTA images and corresponding ground truth multi-label segmentation maps. In some embodiments, multi-label segmentation maps generated by a deep neural network may be stored in CCTA image data 312. In some embodiments, CCTA image data 312 is not disposed at the CCTA image processing system 302.

Non-transitory memory 306 further includes parametric curve module 314, which may be configured to determine one or more parametric curves along a centerline of a branch of a coronary tree imaged by a 3D CCTA image. In some embodiments, parametric curve module 314 comprises instructions for determining one or more pre-defined/pre-determined parameters at each point along a centerline of a branch of a coronary tree, and producing a distinct parametric curve for each pre-determined parameter. In one embodiment, parametric curve module 314 may receive a 3D multi-label segmentation map, comprising a plurality of probability scores for a plurality of anatomical classes for each voxel (or sub-voxel, in the case of super resolution) of a 3D CCTA image, and may determine one or more of lumen radius, plaque thickness, vessel wall thickness, etc. at each point along a centerline of a branch of the coronary tree included within the 3D CCTA image. Parametric curve module 314 may include definitions of the one or more pre-defined parameters, and one or more algorithms for calculating the parameters using multi-label segmentation maps. In some embodiments, parametric curve module 314 is not disposed at the CCTA image processing system 302.

Non-transitory memory 306 further includes lesion detection module 316, which may be configured to receive one or more 1D parametric curves generated by parametric curve module 314, and determine if one or more lesions are present. In response to a determination that one or more lesions are present, lesion detection module 316 may include instructions for determining a location and severity score for each of the one or more lesions. Lesion detection module 316 may include one or more pre-defined criteria for detection of lesions using 1D parametric curves. In some embodiments, lesion detection module 316 may include one or more pre-defined thresholds, wherein lesion detection module 316 may determine that a lesion is present in a 1D parametric curve based on a comparison between the 1D parametric curve and the pre-defined thresholds. In some embodiments, lesion detection module 316 is not disposed at CCTA image processing system 302.

CCTA image processing system 302 may further include user input device 324. User input device 324 may comprise one or more of a touchscreen, a keyboard, a mouse, a trackpad, a motion sensing camera, or other device configured to enable a user to interact with and manipulate data within CCTA image processing system 302. In one example, user input device 324 may enable a user to make a selection of a 3D CCTA image to detect lesions within, using a method, such as method 500 discussed below. In some embodiments, a user may generate a ground truth multi-label segmentation map using user input device 324.

Display device 326 may include one or more display devices utilizing virtually any type of technology. In some embodiments, display device 326 may comprise a computer monitor, and may display 3D CCTA images, 3D multi-label segmentation maps, 1D parametric curves, locations of detected lesions, and severity scores of detected lesions. Display device 326 may be combined with processor 304, non-transitory memory 306, and/or user input device 324 in a shared enclosure, or may be peripheral display devices and may comprise a monitor, touchscreen, projector, or other display device known in the art, which may enable a user to view CCTA images produced by a CCTA imaging system, and/or interact with various data stored in non-transitory memory 306.

It should be understood that CCTA image processing system 302 shown in FIG. 3 is for illustration, not for limitation. Another appropriate image processing system may include more, fewer, or different components.

Turning to FIG. 4, a schematic of a convolutional neural network (CNN) 400, for mapping a 3D CCTA image to a 3D multi-label segmentation map is shown, in accordance with an exemplary embodiment. The 3D multi-label segmentation maps output by CNN 400 may comprise a 3D array of probability scores, corresponding to the 3D array of voxel intensity values in the input 3D CCTA image. Each voxel of the input 3D CCTA image may be mapped to a plurality of probability scores corresponding to a plurality of pre-defined anatomical classes, wherein the probability score for each anatomical class indicates a likelihood of a voxel to which the probability score was assigned, belonging to the anatomical class. In one example, a first voxel of a 3D CCTA image may be mapped to a first probability score and a second probability score in a 3D multi-label segmentation map, wherein the first probability score indicates a probability that the first voxel of the 3D CCTA images represents a first anatomical class (e.g., lumen), and the second probability score indicates a probability that the first voxel of the 3D CCTA image represents a second anatomical class (e.g., plaque), wherein the first and second anatomical classes are distinct.

In some embodiments, CNN 400 may comprise a greater number of outputs than inputs, enabling each voxel of an input 3D CCTA image to be split into a plurality of sub-voxels, and a probability score/classification score, for each anatomical class, may be determined for each sub-voxel, thereby producing an output 3D multi-label segmentation map with a greater resolution than the native resolution of the input CCTA image.

CNN 400 comprises a U-net architecture, which may be divided into an encoder portion (descending portion, elements 402-430) and a decoder portion (ascending portion, elements 432-456). CNN 400 is configured to receive 3D CCTA image data of a heart/coronary tree at input layer 402, comprising a plurality of voxel intensity values, and map the input 3D CCTA image data to a 3D multi-label segmentation map of the heart/coronary. CNN 400 transforms/maps the received 3D CCTA image data by performing a series of convolutions, activations, down sampling operations, and up-sampling operations, and produces a 3D multi-label segmentation map based on output from output layer 456.

The various elements and operations of CNN 400 are labeled in legend 458. As indicated by legend 458, CNN 400 includes a plurality of feature maps (and/or copied feature maps), wherein each feature map may receive input from either an external file, or a previous feature map, and may transform/map the received input to output to produce a next feature map. Each feature map may comprise a plurality of neurons, where in some embodiments, each neuron may receive input from a subset of neurons of a previous layer/feature map, and may compute a single output based on the received inputs, wherein the output may be propagated to a subset of the neurons in a next layer/feature map. A feature map may be described using spatial dimensions, such as length, width, depth, and hyper depth (which may correspond to features of each of voxel of the input image/volume), wherein the dimensions refer to the number of neurons comprising the feature map (e.g., the number of neurons along a length, the number of neurons along a width, the number of neurons along a depth, and the number of neurons along a hyper depth of a specified feature map).

In some embodiments, the neurons of the feature maps may compute an output by performing a dot product of received inputs using a set of learned weights (each set of learned weights may herein be referred to as a filter), wherein each received input has a unique corresponding learned weight, wherein the learned weight was learned during training using a plurality of training data pairs.

The transformations/mappings performed by each feature map are indicated by arrows, wherein each type of arrow corresponds to a distinct transformation, as indicated by legend 458. Rightward pointing solid black arrows indicate 3×3×3 convolutions with stride of one, wherein output from a 3×3×3 grid of feature channels of an immediately preceding feature map are mapped to a single feature channel of a current feature map. Each 3×3×3 convolution may be followed by an activation function, wherein, in one embodiment, the activation function comprises a rectified linear unit (ReLU).

Downward pointing hollow arrows indicate 2×2×2 max pooling, wherein the max value from a 2×2×2 grid of feature channels is propagated from an immediately preceding feature map to a single feature channel of a current feature map, thereby resulting in an 8-fold reduction in spatial resolution of the immediately preceding feature map. In some examples, this pooling occurs for each feature independently.

Upward pointing hollow arrows indicate 2×2×2 up-convolutions, which comprise mapping output from a single feature channel of an immediately preceding feature map to a 2×2×2 grid of feature channels in a current feature map, thereby increasing the spatial resolution of the immediately preceding feature map 8-fold.

Rightward pointing dash-tailed arrows indicate copying and cropping of a feature map for concatenation with another, later occurring, feature map. Cropping enables the dimensions of the copied feature map to match the dimensions of the feature map with which the copied feature map is to be concatenated. It will be appreciated that when the size of the first feature map being copied and the size of the second feature map to be concatenated with the first feature map are equal, no cropping may be performed.

Rightward pointing arrows with hollow elongated triangular heads indicate a 1×1×1 convolution, in which each feature channel in an immediately preceding feature map is mapped to a single feature channel of a current feature map, or in other words, wherein a 1-to-1 mapping of feature channels between an immediately preceding feature map and a current feature map occurs.

Rightward pointing arrows with chevron heads indicate incorporation of Gaussian noise into a received input feature map.

Rightward pointing arrows with arcuate hollow heads indicate batch normalization operations, wherein a distribution of activations of an input feature map are normalized.

Rightward pointing arrows with a short hollow triangular head indicates a dropout operation, wherein random or pseudo-random dropout of input neurons (as well as their inputs and outputs) occurs during training.

In addition to the operations indicated by the arrows within legend 458, CNN 400 includes solid filled rectangles corresponding to feature maps, wherein feature maps comprise a height (top to bottom length as shown in FIG. 4, corresponds to a y spatial dimension in an x-y plane), width (not shown in FIG. 4, assumed equal in magnitude to height, corresponds to an x spatial dimension in an x-y plane), and depth (a left-right length as shown in FIG. 4, corresponds to the number of features within each feature channel). Likewise, CNN architecture 400 includes hollow (unfilled) rectangles, corresponding to copied and cropped feature maps, wherein copied feature maps comprise height (top to bottom length as shown in FIG. 4, corresponds to a y spatial dimension in an x-y plane), width (not shown in FIG. 4, assumed equal in magnitude to height, corresponds to an x spatial dimension in an x-y plane), and depth (a length from a left side to a right side as shown in FIG. 4, corresponds to the number of features within each feature channel).

Starting at 3D CCTA image 402 (herein also referred to as an input layer), data corresponding to a 3D CCTA image may be input and mapped to a first set of features. In one embodiment, CNN 400 comprises one neuron for each feature, of each voxel, of the input 3D CCTA image. For example, for an input 3D CCTA image comprising 100×100×100 voxels, with 3 color channels per voxel, input layer 402 may comprise 100×100×100×3 input neurons. The 3D CCTA image may have been acquired by a CCTA imaging system, such as CCTA imaging system 100, shown in FIG. 1, or by an imaging system, such as imaging system 200, shown in FIG. 2. In some embodiments, the input data is pre-processed (e.g., normalized) before being processed by CNN 400. In some embodiments, the input data is an array of intensity values for a plurality of voxels.

Output layer 456 may comprise a plurality of output neurons, wherein each output neuron may correspond to a distinct region in space within the volume imaged by input 3D CCTA image. Output from each output neuron may comprise a probability score/classification score for one or more pre-defined anatomical classes, assigned to a voxel (or sub-voxel) of the input 3D CCTA image. For example, the output of an output neuron may indicate a probability that a voxel (or sub-voxel) of an input 3D CCTA image is part of a vessel wall, a fibrous cap of a plaque, a lipid core of a plaque, etc. In some embodiments, output layer 456 may comprise a greater spatial resolution than input layer 402. For example, if an input layer comprises 100×100×100×F input neurons, where F is the number of features per voxel, output layer 456 may comprise 200×200×200×O, where O is the number of anatomical classes, and where each voxel of the input image has been divided into four sub-voxels in the output image.

The weights (and biases) of the convolutional layers in the neural network 400 are learned during training, as will be discussed in more detail with reference to FIG. 6 below. Briefly, a loss function is defined to reflect the difference between the multi-label segmentation map output by CNN 400 and a corresponding ground truth multi-label segmentation map. The loss may be backpropagated through the layers of CNN 400, starting from the output layer 456, and proceeding to input layer 402, wherein at each layer a gradient of the loss function is determined for each parameter of the layer, and each parameter is updated based on the determined gradient.

It will be appreciated that the current disclosure encompasses neural network architectures comprising one or more regularization layers, including batch normalization layers, dropout layers, Gaussian noise layers, and other regularization layers known in the art of machine learning which may be used during training to mitigate overfitting and increase training efficiency while reducing training duration. Regularization layers are used during training and deactivated or removed during post training implementation of the CNN. These layers may be interspersed between the layers/feature maps shown in FIG. 4, or may replace one or more of the shown layers/feature maps.

It should be understood that the architecture and configuration of CNN 400 shown in FIG. 4 is for illustration, not for limitation. Any appropriate neural network can be used herein for predicting anatomical ROI attribute maps from MR calibration images, such as ResNet, recurrent neural networks, General Regression Neural Network (GRNN), etc. One or more specific embodiments of the present disclosure are described above in order to provide a thorough understanding. These described embodiments are only examples of systems and methods for determining multi-label segmentation maps from 3D CCTA images using a deep neural network. The skilled artisan will understand that specific details described in the embodiments can be modified when being placed into practice without deviating the spirit of the present disclosure.

Referring to FIG. 5, a flow chart of a method 500 for detecting lesions in 3D CCTA images of coronary trees using deep neural networks is shown, according to an exemplary embodiment. Method 500 may be implemented by the CCTA imaging system 100, imaging system 200, and/or CCTA image processing system 302.

Method 500 begins at operation 502, where a 3D CCTA image is acquired by a CCTA imaging system. The 3D CCTA image may comprise a plurality of voxels, wherein each voxel includes an intensity value. The 3D CCA image may comprise a 3D CCTA image of a coronary tree.

At operation 504, the 3D CCTA image is input into an input layer of a trained deep neural network, which maps 3D CCTA image to a multi-label segmentation map. In some embodiments, the deep neural network is a CNN, such as CNN 400 illustrated schematically in FIG. 4. In some embodiments, each voxel intensity value of the 3D CCTA image is input into a distinct neuron of the input layer of the deep neural network. The input intensity values are propagated through the one or more hidden layers of the deep neural network, until reaching an output layer of the, wherein the neurons of the output layer output a plurality of probability scores, corresponding to a plurality of anatomical classes, for each voxel or sub-voxel of the input 3D CCTA image. The relationship between two adjacent layers of the deep neural network, other than the input layer, may be described as follows:

$$Y_j = f\left(\sum_{i=1}^{n} W_{ji} X_i + B_j\right)$$

Where $X_i$ is the output of the i-th neuron of the preceding layer, $Y_j$ is the j-th neuron of the subsequent layer, $W_{ji}$ is the weight, and $B_j$ is the bias. In some embodiments, the activation function $f$ is a rectified linear unit (ReLU) function, for example, plain ReLU function, leaky ReLU function, parametric ReLU function, etc.

In some embodiments, the output from the output layer of the deep neural network is of a same dimension as the input 3D CCTA image. In some embodiments, the dimension of the output from the output layer comprises a larger dimension than the input 3D CCTA image, in other words, the output multi-label segmentation map may comprise a super-resolution segmentation map, having a greater spatial resolution than the input 3D CCTA image. The multi-label segmentation map may comprise a 3D grid/array of entries, wherein each entry comprises one probability score for each of a set of pre-defined anatomical classes. Each entry may correspond to a unique spatial region within the input 3D CCTA image, and thereby each entry may designate a series of probability scores for each of a plurality of anatomical classes for each spatial region within the 3D CCTA image.

At operation 506, a plurality of 1D parametric curves are generated for each branch of the coronary tree imaged by the input 3D CCTA image. In some embodiments, operation 506 comprises identifying each branch of the coronary tree, determining a centerline for each branch of the coronary tree, and computing a plurality of 1D parametric curves for each point along the centerlines of each branch of the coronary tree. In one example, 1D parametric curves may show a plaque thickness, a lumen radius, a plaque density, a vessel wall thickness, a lipid core thickness, or other pre-defined parameters which may be derived from the multi-label segmentation map, as a function of length along a centerline of a coronary branch, or as a function of angle around a point of a centerline of the coronary branch.

In some examples, the 1D parametric curves may show a parameter as a function of length along the centerline of a coronary branch, and/or as a function of angle around the centerline of the coronary branch at a given point along the centerline. In one example, the 1D parametric curves indicate a lumen radius, plaque thickness, or other pre-determined parameter, for each angle around a point along a centerline of a branch of the coronary tree. For a point along the centerline of the coronary branch, an average, maximum, and minimum for each pre-determined parameter, may be determined using the parameter values for each angle determined at the point.

The parameters may be determined at pre-specified intervals along a branch of a coronary tree by taking a cross section of the multi-label segmentation map, through the branch, perpendicular to a direction of extent of the branch, and determining the parameters at each angle around the centerline. In one example, a cross section of a multi-label segmentation map may be taken at a point along a centerline of a branch of a coronary tree. The cross section may show the lumen as a substantially circular opening, padded by vessel wall, and plaque. A radius of the lumen may be determined at each angle around the centerline, that is, as the lumen cross section may not be exactly circular, and therefore different radii may be determined at different angles around the centerline. Similarly, vessel wall, plaque, lipid core, etc. may not be symmetrical about the centerline (as seen in cross section through a coronary branch), and therefore these asymmetrical parameters may be assessed at each angle around the centerline. An average of each parameter may be determined for each cross section of a coronary branch, by averaging the parameter values at each angle around the centerline for the cross section. The minimum and maximum values for each parameter may be similarly determined for each cross section of a coronary branch.

The 1D parametric curves may be generated based on the multi-label segmentation map produced in operation 506. For example, a lumen radius at a point along a centerline (longitudinal axis) of a branch of a coronary tree may be determined using a multi-label segmentation map by determining a number of voxels classified as lumen along a line passing through, and perpendicular to, the centerline, and multiplying the number of voxels by a spatial size of each voxel.

At operation 508, the plurality of 1D parametric curves are used to determine if one or more lesions are present along one or more of the branches of the coronary tree. Further, at operation 508, in response to a detected lesion, the location of the lesion, including the start and stop points of the lesion along a branch of the coronary tree may be determined. In some embodiments, CCTA image processing system 302 may determine a lesion is present in a branch of a coronary tree responsive to a lumen radius decreasing below a threshold lumen radius, and further responsive to a plaque thickness exceeding a threshold plaque thickness, along section/length of a branch of the coronary tree. The location of a detected lesion, including the start and stop points of the lesion in the branch of the coronary, tree may be determined based on the lumen radius and plaque thickness thresholds. In one example, a point along a centerline of a branch of a coronary tree may be set as the start point of a lesion, in response to an average plaque thickness at the point increasing beyond a plaque thickness threshold, and further in response to an average lumen radius at the point decreasing to below a lumen radius threshold. Similarly, a point along a centerline of a branch of a coronary tree may be set as the end point of a lesion in response to an average plaque thickness at the point decreasing to below a plaque thickness threshold, and further in response to an average lumen radius at the point increasing to above a lumen radius threshold.

At operation 510, severity scores for the lesions detected at operation 508 are determined. Severity score(s) for each of the detected lesion(s) may be determined based on one or more values of the plurality of 1D parametric curves in the region(s) of the detected lesion(s). In some embodiments, a severity score for a detected lesion may be based on a lumen radius and plaque thickness in a region of the lesion. In some embodiments, a severity score may be determined for a lesion based on the plurality of 1D parametric curves by increasing a severity score as a lumen radius in a region of the lesion decreases below a lumen radius threshold. In some embodiments, a severity score is determined based on a thickness of plaque in a region of the lesion.

At operation 512, the detected lesions are displayed to a user via a display device, along with computed severity scores for each of the detected lesions. In some embodiments, a detected lesion is shown to a user by overlaying an indication region on the input 3D CCTA image. In some embodiments, a detected lesion is displayed to a user using the plurality of 1D parametric curves, wherein a region corresponding to the one or more detected lesions is highlighted, boxed, or otherwise distinguished from other regions of the 1D parametric curves.

In this way, method 500 enables automatic, rapid, and robust detection and designation of coronary lesions using deep neural networks. A technical effect of automatically labeling voxels of a 3D CCTA image using a trained deep neural network is that a time of diagnosis, and a consistency of diagnosis of coronary lesions, may be increased. Further, a technical effect of automatically determining a severity score for the one or more detected coronary lesions based on 1D parametric curves generated using the multi-label segmentation map, is that a more consistent, quantitative severity score scheme may be employed rapidly, without relying on manual assessment by expert cardiologists.

Figure 6:
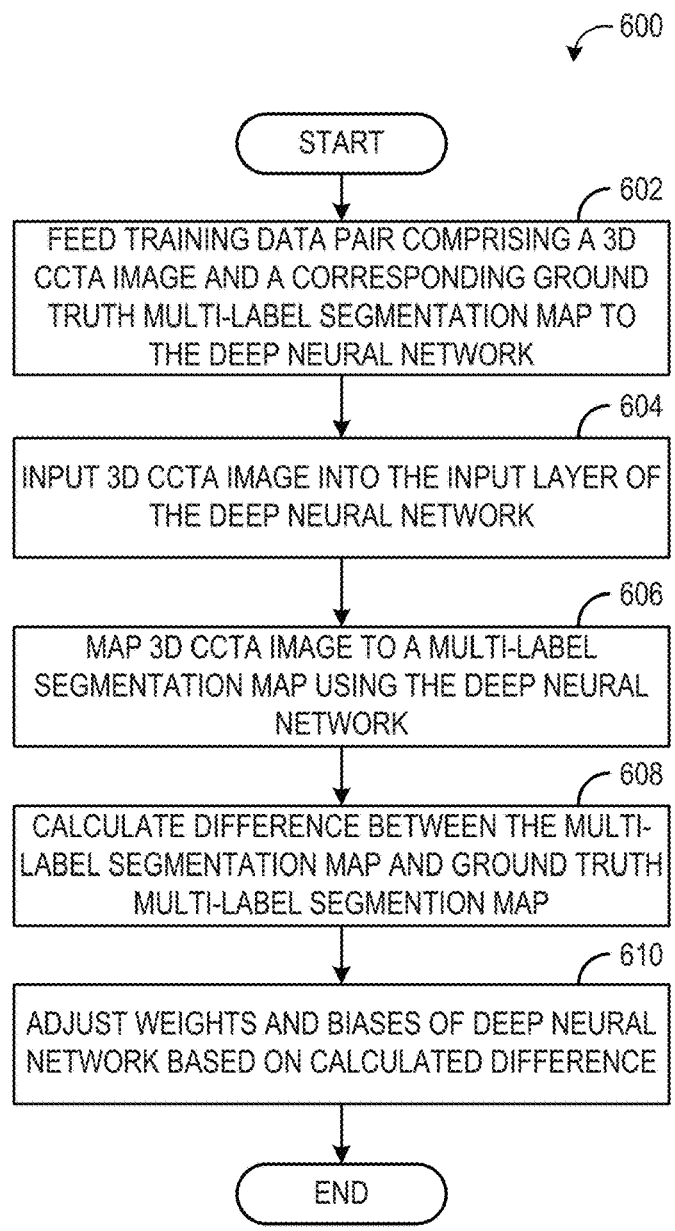
FIG. 6 is a flow chart illustrating a method for training a deep neural network to determine a multi-label segmentation map from a 3D CCTA image, according to an exemplary embodiment.
Figure 7:
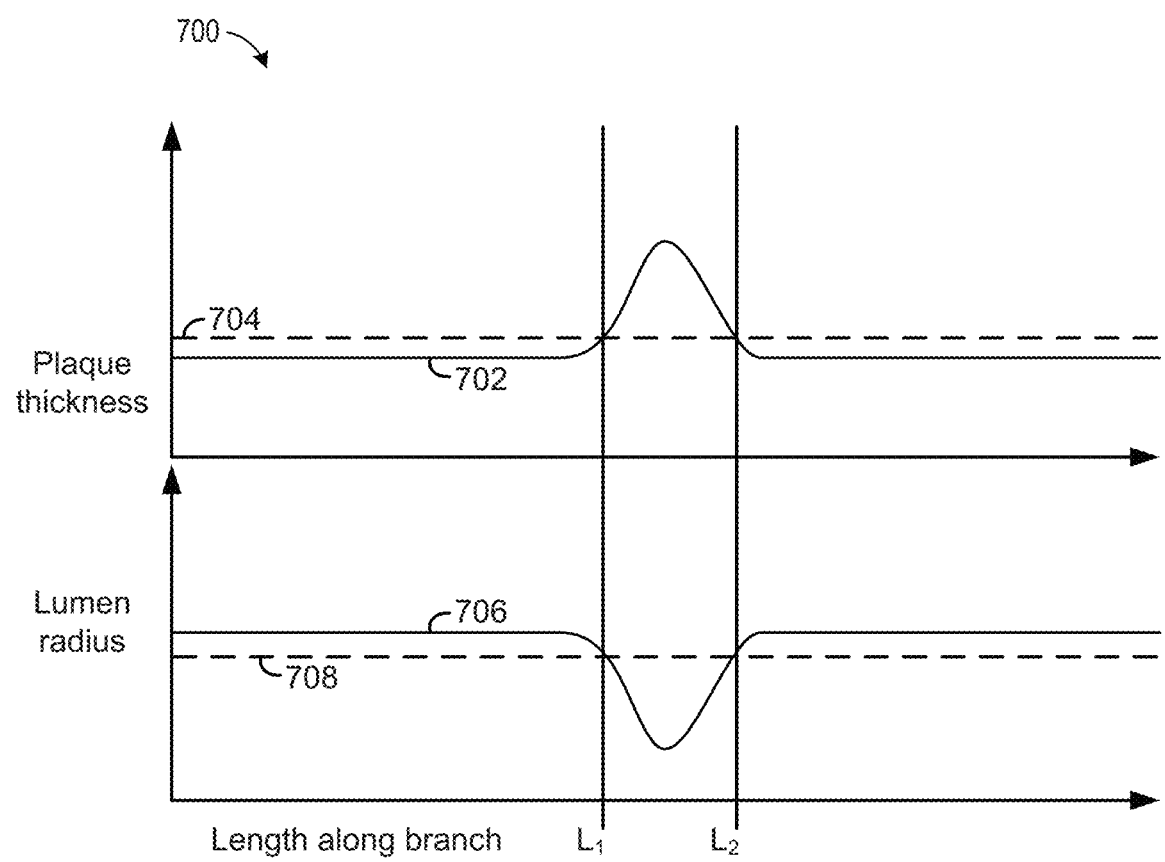
FIG. 7 is a prophetic example of 1D parametric curves which may be generated from a multi-label segmentation map for a branch of a coronary tree.

Referring to FIG. 6, a flow chart of a method 600 for training a deep neural network (such as CNN 400 shown in FIG. 4) is shown, according to an exemplary embodiment. Method 600 may be implemented by one or more of the above discussed systems. In some embodiments, method 600 may be implemented by training module 310, stored in non-transitory memory 306 of CCTA image processing system 302.

Method 600 begins at operation 602, where a training data pair, from a plurality of training data pairs, is fed to a deep neural network, wherein the training data pair comprises a 3D CCTA image of a coronary tree and a corresponding ground truth multi-label segmentation map of the coronary tree. In some embodiments, the training data pair, and the plurality of training data pairs, may be stored in CCTA image data 312. In other embodiments, the training data pair may be acquired via communicative coupling between the CCTA image processing system and an external storage device, such as via Internet connection to a remote server. In some embodiments, the ground truth multi-label segmentation map is generated manually via expert curation.

At operation 604, the 3D CCTA image of the training data pair is input into an input layer of the deep neural network. In some embodiments, the 3D CCTA image is input into an input layer of a CNN. In some embodiments, each voxel intensity value of the 3D CCTA image is input into a distinct neuron of the input layer of the deep neural network.

At operation 606, the deep neural network maps the input 3D CCTA image to a 3D multi-label segmentation map by propagating the input 3D CCTA image from the input layer, through one or more hidden layers, until reaching an output layer of the deep neural network. In some embodiments the output of the deep neural network comprises a 3D matrix of entries, wherein each entry corresponds to a distinct voxel of the input 3D CCTA image, and wherein each entry comprises a plurality of probability scores/label scores for each of a plurality of pre-determined anatomical classes.

At operation 608, the difference between the predicted multi-label segmentation map and the ground truth multi-label segmentation map of the training data pair is calculated.

At operation 610, the weights and biases of the deep neural network are adjusted based on the difference between the predicted multi-label segmentation map and the ground truth multi-label segmentation map. The difference (or loss), as determined by the loss function, may be back propagated through the neural learning network to update the weights (and biases) of the convolutional layers. In some embodiments, back propagation of the loss may occur according to a gradient descent algorithm, wherein a gradient of the loss function (a first derivative, or approximation of the first derivative) is determined for each weight and bias of the deep neural network. Each weight (and bias) of the deep neural network is then updated by adding the negative of the product of the gradient determined (or approximated) for the weight (or bias) with a predetermined step size. Method 600 may then end. It will be noted that method 600 may be repeated until the weights and biases of the deep neural network converge, or the rate of change of the weights and/or biases of the deep neural network for each iteration of method 500 are under a threshold.

In this way, method 600 enables a deep neural network to be trained to predict a multi-label segmentation map from an input 3D CCTA image of a coronary tree.

Turning to FIG. 7, an example of a plurality of 1D parametric curves 700 generated for a branch of a coronary tree using a multi-label segmentation map of the coronary tree, is shown. The plurality of 1D parametric curves 700 may be generated by one or more of the systems described above, using a multi-label segmentation map generated by a deep neural network using one or more 3D CCTA images. In one embodiment, parametric curve module 314, stored in non-transitory memory 306 of CCTA image processing system 302, may produce the plurality of 1D parametric curves 700 from a multi-label segmentation map produced by a deep neural network, such as deep neural network 400, illustrated in FIG. 4.

1D parametric curves 700 include a plaque thickness 702, and a lumen radius 706, determined at points along a centerline of one branch of a coronary tree. In other words, 1D parametric curves 700 comprise plaque thickness 702 and lumen radius 706, determined as a function of distance along a branch of a coronary tree. In one example, plaque thickness 702 may comprise an average plaque thickness, determined at each point along a centerline of a branch of the coronary tree, determined as an average of the plaque thickness at each angle around each point of the centerline. Similarly, lumen radius 706 may comprise an average lumen radius, determined at each point along the centerline, as the average of each lumen radius determined for each angle around the centerline.

Although 1D parametric curves 700 include plaque thickness 702, and lumen radius 706, for a single coronary branch of a coronary tree, it will be appreciated that the current disclosure provides for 1D parametric curves determined for more than one branch of a coronary tree (e.g., a plurality of 1D parametric curves similar to those shown in FIG. 7 may be determined for each of a plurality of branches of a coronary tree), and wherein the 1D parametric curves may comprise substantially any pre-defined parameter herein disclosed, which may be derived from the multi-label segmentation maps as a function of distance along a centerline of a branch of a coronary tree, including radius, diameter, thickness, area, and volume of any of the labeled components (lumen, vessel wall, plaque, lipid core, fibrous cap, etc.) included in the 3D multi-label segmentation map, determined at a point, or at a running average of points, along a centerline of a branch of a coronary tree. In some embodiments, 1D parametric curves determined for one or more branches of a coronary tree may include, lumen volume, lipid core thickness, plaque volume, plaque area, lumen tortuosity, vessel wall thickness, and plaque roughness/shape.

1D parametric curves 700 include plaque thickness 702, showing the plaque thickness at each point along a centerline of the branch of the coronary tree. In some embodiments, plaque thickness 702 may be determined using a 3D multi-label segmentation map, such as those describe throughout the current disclosure, according to a pre-determined/pre-defined algorithm, and therefore, plaque thickness may be referred to as pre-determined parameter. In one embodiment, determining a plaque thickness at a point along a centerline of a branch of a coronary tree included in a 3D multi-label segmentation map comprises, fitting a centerline through each distinct path/branch of a coronary tree, by minimizing a sum of squared distances between the centerline and each voxel of the multi-label segmentation map classified as vessel wall within a plane perpendicular to a longitudinal extent of the coronary branch, and at each point along each centerline of each of the branches, determining a cross sectional thickness of plaque, wherein the cross section is perpendicular to a direction of extent of the centerline. In some embodiments, determining a cross sectional thickness of plaque at a point along a centerline of a branch of a coronary tree comprises determining a number of voxels with a plane perpendicular to a direction of extent of the centerline, and multiplying the number of voxels by a constant, wherein the constant is the ratio between length and voxel (e.g., 1 mm/voxel).

Plaque thickness 702 is shown along with plaque thickness threshold 704, wherein plaque thickness threshold 704 comprises a pre-determined plaque thickness threshold. Plaque thickness threshold 704 may be determined based on one or more parameters of the coronary branch for which 1D parametric curves are determined. In one embodiment, plaque thickness threshold 704 may comprise a pre-determined fraction of a current lumen radius of the current branch, or a pre-determined fraction of an average lumen radius for the current branch. In some embodiments, plaque thickness threshold 704 may comprise a constant value. At $L_1$, plaque thickness 702 increases beyond plaque thickness threshold 704, which in some embodiments, may indicate a starting point of a coronary lesion within the current coronary branch. At $L_2$, plaque thickness 702 decreases to below plaque thickness threshold 704, which in some embodiments, may indicate a stopping/termination point of the coronary lesion. In some examples, a location of a lesion may be specified by the start and stop point of the lesion, such as may be indicated by $L_1$ and $L_2$. In some embodiments, a severity score for the coronary lesion indicated between $L_1$ and $L_2$ may be determined based on the extent beyond the plaque thickness threshold 704 to which plaque thickness 702 extends, wherein the severity score may increase as the plaque thickness 702 increases beyond plaque thickness threshold 704.

1D parametric curves 700 further include lumen radius 706, showing the lumen radius at each point along the centerline of the branch of the coronary tree. In some embodiments, lumen radius 706 may be determined using a 3D multi-label segmentation map, according to pre-determined instructions, and therefore, lumen radius may be referred to as pre-determined parameter. In one embodiment, determining a lumen radius at a point along the centerline of a branch of a coronary tree included in a 3D multi-label segmentation map comprises, fitting a centerline through each distinct path/branch of a coronary tree, by minimizing a sum of squared distances between the centerline and each voxel of the multi-label segmentation map classified as vessel wall within a plane perpendicular to a longitudinal extent of the coronary branch, and at each point along each centerline of each of the branches of the coronary tree, determining a cross sectional diameter/radius of the lumen, wherein the cross section is perpendicular to a direction of extent of the centerline. In some embodiments, determining a lumen radius at a point along a centerline of a branch of a coronary tree using a multi-label segmentation map comprises, determining a number of voxels in the multi-label segmentation map classified as lumen within a plane perpendicular to a direction of extent of the centerline, and multiplying the number of voxels by a constant, wherein the constant is the ratio between length and voxel (e.g., 1 mm/voxel).

Shown alongside lumen radius 706 is lumen radius threshold 708. Lumen radius threshold 708 may be determined based on one or more parameters of the coronary branch for which 1D parametric curves 700 are determined. In one embodiment, lumen radius threshold 708 may comprise a pre-determined fraction of a current lumen radius of the current branch, or a pre-determined fraction of an average lumen radius for the current branch. In some embodiments, lumen radius threshold 708 may comprise a constant, pre-determined value. At $L_1$, lumen radius 706 decreases to below lumen radius threshold 708, which in some embodiments, may indicate a starting point of a coronary lesion within the current coronary branch. At $L_2$, lumen radius 706 increases above lumen radius threshold 708, which in some embodiments, may indicate a stopping/termination point of the coronary lesion. In some embodiments, a severity score for the coronary lesion indicated between $L_1$ and $L_2$ may be determined based on the extent beyond the lumen radius threshold 708 to which lumen radius 706 extends, wherein the severity score may increase as the lumen radius 706 decreases below the lumen radius threshold 708.

In some embodiments, a coronary lesion may detected responsive to both plaque thickness 702 increasing above plaque thickness threshold 704, and lumen radius 706 decreasing to below the lumen radius threshold 708, in a same region along a branch of the coronary tree, such as between $L_1$ and $L_2$, in FIG. 7.

Turning to FIG. 8, three examples of CCTA images, and corresponding multi-label segmentation maps, are shown.

Specifically, FIG. 8 shows first CCTA image 802, second CCTA image 806, and third CCTA image 810, which may be mapped via a 3D convolutional neural network (e.g., CNN 400), to first multi-label segmentation map 804, second multi-label segmentation map 808, and third multi-label segmentation map 812, respectively. Each of the multi-label segmentation maps (804, 808, and 812), include labeled regions of plaque (pink), lumen (greenish-blue), lipid core (yellow), and external tissue (blue), which are clearly indicated by the associated, colored labels. The CCTA images of FIG. 8 may be acquired by an imaging system, such as CCTA imaging system 100, shown in FIG. 1. Further, the multi-label segmentation maps (804, 808, and 812) may be used according to one or more methods disclosed herein, to generate 1D parametric curves, from which a location and severity of coronary lesions may be ascertained.

First CCTA image 802 shows a first branch of a coronary tree. First CCTA image 802 may be mapped to first multi-label segmentation map 804 via a trained convolutional neural network. First multi-label segmentation map 804 includes a coronary lesion start point 816, and a coronary lesion end point 818, with plaque 814 and lumen 820 therebetween. Plaque 814 comprises voxels of first CCTA image 802 classified as plaque (shown in pink), while lumen 820 comprises voxels of first CCTA image 802 classified as lumen (shown in greenish-blue). The region of the coronary branch bounded by start point 816 and end point 818 comprises an identified coronary lesion, having a reduced lumen radius therein, indicating a region of plaque buildup along the branch of the coronary tree.

Second CCTA image 806 shows a second branch of a coronary tree including a lesion. Second CCTA image 806 may be mapped to second multi-label segmentation map 808 via a trained convolutional neural network. Second multi-label segmentation map 808 includes a coronary lesion start point 822, and a coronary lesion end point 830, with lumen 824, plaque 826, and external tissue 828, shown therebetween. Lumen 824 comprises voxels of second CCTA image 806 classified/labeled as lumen (greenish-blue), plaque 826 comprises voxels of second CCTA image 806 classified as plaque (shown in pink), while external tissue 828 comprises voxels of second CCTA image 806 classified as external tissue (blue). The region of the second coronary branch bounded by start point 822 and end point 830 comprises an identified coronary lesion, having a reduced lumen radius therein, indicating a region of plaque buildup along the branch of the coronary tree.

Third CCTA image 810 shows a third branch of a coronary tree including a lesion. Third CCTA image 810 may be mapped to third multi-label segmentation map 812 via a trained convolutional neural network. Third multi-label segmentation map 812 includes a coronary lesion start point 832, and a coronary lesion end point 840, with lumen 834, lipid core 836, and plaque 838, shown therebetween. Lumen 834 comprises voxels of third CCTA image 810 classified/labeled as lumen (greenish-blue), lipid core 836 comprises voxels of third CCTA image 810 classified/labeled as lipid core (yellow), and plaque 838 comprises voxels of third CCTA image 810 classified/labeled as plaque (shown in pink). The region of the third coronary branch bounded by start point 832 and end point 840 comprises an identified coronary lesion, having a reduced lumen radius therein, indicating a region of plaque buildup along the branch of the coronary tree.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A method comprising:
acquiring a 3D cardiac computed tomography and angiography (CCTA) image of a coronary tree;
mapping the 3D CCTA image to a multi-label segmentation map with a trained deep neural network;
generating a plurality of 1D parametric curves for a branch of the coronary tree using the multi-label segmentation map;
determining a location of a lesion in the branch of the coronary tree using the plurality of 1D parametric curves, wherein determining the location of the lesion in the branch of the coronary tree using the plurality of 1D parametric curves comprises determining start and stop points of the lesion in the branch of the coronary tree based on the plurality of 1D parametric curves; and
determining a severity score for the lesion based on the plurality of 1D parametric curves,
wherein generating the plurality of 1D parametric curves for the branch of the coronary tree using the multi-label segmentation map comprises determining values for each of a plurality of pre-defined parameters for each point along a centerline of the branch of the coronary tree, wherein the plurality of pre-defined parameters include one or more of lipid core thickness, vessel wall thickness, lumen radius, and lumen tortuosity.

2. The method of claim 1, wherein the multi-label segmentation map comprises a plurality of probability scores for each voxel of the 3D CCTA image, for a plurality of anatomical classes.

3. The method of claim 2, wherein the plurality of pre-defined parameters are determined using a cross section of the multi-label segmentation map at each point along the centerline of the branch of the coronary tree.

4. The method of claim 2, wherein the plurality of anatomical classes comprise:

lumen;
media;
lipid core;
fibrous cap;
calcium; and
external tissue.

5. The method of claim 1, wherein at each point along the centerline, minimum, maximum, and average values for one or more of lipid core thickness, plaque thickness, plaque area, plaque density, vessel wall thickness, lumen radius, lumen tortuosity, and lumen volume, are determined for each angle around the centerline.

6. The method of claim 1, wherein determining the location of the lesion in the branch of the coronary tree using the plurality of 1D parametric curves comprises:
responding to a plaque thickness being greater than a plaque thickness threshold in a region of the branch by:
concluding the region is the location of the lesion.

7. The method of claim 6, wherein determining the severity score for the lesion based on the plurality of 1D parametric curves comprises, determining the severity score based on a lipid core thickness in the region.

8. The method of claim 1, wherein a resolution of the multi-label segmentation map is greater than a native resolution of the 3D CCTA image.

9. The method of claim 1, wherein the trained deep neural network comprises a 3D convolutional neural network.

10. A method comprising:
training a deep neural network to map 3D CCTA images to 3D multi-label segmentation maps;
receiving a first 3D CCTA image;
mapping the first 3D CCTA image to a 3D multi-label segmentation map using the trained deep neural network;
determining a plurality of 1D parametric curves for a coronary artery included in the first 3D CCTA image using the 3D multi-label segmentation map; and
determining a location of a lesion in a branch of a coronary tree using the plurality of 1D parametric curves, wherein determining the location of the lesion in the branch of the coronary tree using the plurality of 1D parametric curves comprises determining start and stop points of the lesion in the branch of the coronary tree based on the plurality of 1D parametric curves,
wherein determining the plurality of 1D parametric curves for the coronary artery comprises determining values for each of a plurality of pre-defined parameters for each point along a centerline of the branch of the coronary tree, the plurality of pre-defined parameters include lipid core thickness, vessel wall thickness, lumen radius, and lumen tortuosity.

11. The method of claim 10, wherein training the deep neural network comprises feeding a training data pair to the deep neural network, wherein the training data pair includes a second 3D CCTA image and a corresponding ground truth 3D multi-label segmentation map.

12. The method of claim 11, wherein training the deep neural network comprises:
mapping the second 3D CCTA image in the training data pair to a predicted 3D multi-label segmentation map using the deep neural network;
calculating a difference between the predicted 3D multi-label segmentation map and a ground truth 3D multi-label segmentation map; and
adjusting parameters of the deep neural network via backpropagation based on the difference between the predicted 3D multi-label segmentation map and the ground truth 3D multi-label segmentation map.

13. A cardiac computed tomography and angiography (CCTA) imaging system comprising:
an x-ray radiation source;
an x-ray detector array;
a memory storing a trained deep neural network and instructions; and
a processor communicably coupled to the x-ray radiation source, the x-ray detector array, and the memory, and when executing the instructions, configured to:
acquire a 3D CCTA image of a coronary tree using the x-ray radiation source and the x-ray detector array;
map the 3D CCTA image to a multi-label segmentation map with the trained deep neural network;
generate a plurality of 1D parametric curves for a branch of the coronary tree using the multi-label segmentation map; and
determine a location of a lesion in the branch of the coronary tree using the plurality of 1D parametric curves,
wherein the processor is configured to:
generate the plurality of 1D parametric curves for the branch of the coronary tree using the multi-label segmentation map by determining values for each of a plurality of pre-defined parameters along a centerline of the branch of the coronary tree, wherein the plurality of pre-defined parameters are derived from the multi-label segmentation map, wherein the plurality of pre-defined parameters include one or more of lipid core thickness, vessel wall thickness, lumen radius, and lumen tortuosity; and
determine the location of the lesion in the branch of the coronary tree using the plurality of 1D parametric curves by:
comparing the plurality of 1D parametric curves against one or more pre-defined thresholds; and
determining start and stop points of the lesion in the branch of the coronary tree based on one or more of the plurality of 1D parametric curves crossing one or more of the pre-defined thresholds.

14. The system of claim 13, wherein the processor is configured to determine the location of the lesion in the branch of the coronary tree using the plurality of 1D parametric curves by:
responding to both a plaque thickness being greater than a plaque thickness threshold and the lumen radius being less than a lumen radius threshold, in a region of the branch of the coronary tree by:
flagging the region as including the lesion.

15. The system of claim 13, wherein the multi-label segmentation map comprises a plurality of probability scores for each voxel of the 3D CCTA image, for each of a plurality of anatomical classes, wherein the plurality of anatomical classes include one or more of lumen, media, lipid core, fibrous cap, calcium, and external tissue.

16. The system of claim 13, wherein, when executing the instructions, the processor is further configured to:
determine a severity score for the lesion based on the lipid core thickness.

17. The system of claim 16, wherein the system further comprises a display device, and wherein, when executing the instructions, the processor is further configured to display the location of the lesion and the severity score via the display device.

18. The system of claim 14, wherein the lumen radius threshold is determined based on an average lumen radius for the branch of the coronary tree.

\* \* \* \* \*